United States Patent
Kram et al.

(10) Patent No.: US 9,709,547 B2
(45) Date of Patent: Jul. 18, 2017

(54) SENSOR UNIT FOR DETERMINING PROPERTIES OF A LUBRICANT AND MACHINE ELEMENT AND MACHINE ASSEMBLY

(71) Applicant: Schaeffler Technologies AG & Co. KG, Herzogenaurach (DE)

(72) Inventors: Martin Kram, Gerolzhofen (DE); Thomas Drescher, Wachenroth (DE); Stephan Neuschaefer-Rube, Herzogenaurach (DE); Andreas Bill, Nuremberg (DE)

(73) Assignee: SCHAEFFLER TECHNOLOGIES AG & CO. KG, Herzogenaurach (DE)

( * ) Notice: Subject to any disclaimer, the term of this patent is extended or adjusted under 35 U.S.C. 154(b) by 0 days.

(21) Appl. No.: 15/028,151

(22) PCT Filed: Sep. 15, 2014

(86) PCT No.: PCT/DE2014/200473
§ 371 (c)(1),
(2) Date: Apr. 8, 2016

(87) PCT Pub. No.: WO2015/051792
PCT Pub. Date: Apr. 16, 2015

(65) Prior Publication Data
US 2016/0258923 A1    Sep. 8, 2016

(30) Foreign Application Priority Data
Oct. 10, 2013    (DE) .................. 10 2013 220 457

(51) Int. Cl.
*G01J 5/00*    (2006.01)
*G01N 33/28*    (2006.01)
(Continued)

(52) U.S. Cl.
CPC ........ *G01N 33/2888* (2013.01); *G01M 13/04* (2013.01); *G01N 21/3577* (2013.01);
(Continued)

(58) Field of Classification Search
CPC .. G01N 21/3563; G01N 21/359; G01N 21/14; G01N 11/10; G01N 21/31;
(Continued)

(56) References Cited

U.S. PATENT DOCUMENTS 5,194,910 A * 3/1993 Kirkpatrick, Jr. ... G01N 33/2888
250/573
5,394,739 A * 3/1995 Garvey, III ............ G01N 11/14
73/54.15
(Continued)

FOREIGN PATENT DOCUMENTS

DE    102007042254    4/2009
DE    102008019500    4/2009
(Continued)

OTHER PUBLICATIONS

FAG Products for Condition Monitoring, FAG GreaseCheck, Grease Condition Monitoring During Operation, Schaeffler Technologies AG & Co. KG, product information fact sheet, Aug. 2013.
(Continued)

*Primary Examiner* — Kiho Kim
(74) *Attorney, Agent, or Firm* — Volpe and Koenig, P.C.

(57) ABSTRACT

A sensor unit is disclosed for determining properties of a lubricant; for example, a lubricating grease in a rolling bearing. A machine element may include the sensor unit and a machine assembly may include the machine element. The sensor unit includes a sensor housing having a window which can be aligned to the lubricant. A transmitter for emitting electromagnetic radiation through the window and a receiver for receiving electromagnetic radiation which
(Continued)

passes through the window are located in the sensor housing. Evaluating electronics arranged in the sensor housing are electrically connected at least to the receiver. The evaluating unit is designed to generate at least one digital sensor signal. The sensor unit further includes an electrical connection, which is led through the sensor housing and electrically connected to the evaluating electronics in the sensor housing.

10 Claims, 1 Drawing Sheet

(51) Int. Cl.

| | | |
|---|---|---|
| *G01N 21/3577* | (2014.01) | |
| *G01N 21/47* | (2006.01) | |
| *G01N 21/85* | (2006.01) | |
| *G01M 13/04* | (2006.01) | |
| *F16C 19/52* | (2006.01) | |
| *G01N 21/3554* | (2014.01) | |
| *G01N 21/359* | (2014.01) | |
| *G01N 21/552* | (2014.01) | |
| *G01N 21/01* | (2006.01) | |
| *F16C 33/66* | (2006.01) | |

(52) U.S. Cl.
CPC ....... *G01N 21/474* (2013.01); *G01N 21/8507* (2013.01); *G01N 33/2847* (2013.01); *F16C 19/525* (2013.01); *F16C 33/6625* (2013.01); *F16C 2233/00* (2013.01); *G01N 21/359* (2013.01); *G01N 21/3554* (2013.01); *G01N 21/552* (2013.01); *G01N 2021/0143* (2013.01); *G01N 2201/061* (2013.01)

(58) Field of Classification Search
CPC ............. G01N 21/534; G01N 33/2888; G01N 21/3151; G01N 21/532; G01M 15/042
See application file for complete search history.

(56) References Cited

U.S. PATENT DOCUMENTS

| | | | |
|---|---|---|---|
| 6,331,704 B1 | 12/2001 | Owen | |
| 6,582,661 B1 | 6/2003 | Pardue et al. | |
| 7,442,291 B1* | 10/2008 | Discenzo | ............. B01D 35/143 210/443 |
| 8,785,860 B2 | 7/2014 | Kram et al. | |
| 2003/0060984 A1* | 3/2003 | Takezawa | .......... G01N 21/3151 702/28 |
| 2005/0088646 A1* | 4/2005 | Kong | ................... G01N 21/643 356/70 |
| 2009/0145211 A1* | 6/2009 | Schneider | ........... G01M 15/042 73/114.55 |
| 2010/0157304 A1* | 6/2010 | Takahashi | ............... F16C 19/52 356/442 |
| 2010/0208241 A1* | 8/2010 | Franke | .................... F16C 19/52 356/51 |
| 2011/0301489 A1* | 12/2011 | Essex | .................. A61B 5/0531 600/547 |
| 2013/0250281 A1* | 9/2013 | Shirata | ............... G01N 33/2888 356/70 |

FOREIGN PATENT DOCUMENTS

| | | |
|---|---|---|
| DE | 102009037424 | 2/2011 |
| DE | 102010015084 | 10/2011 |
| DE | 102010031919 | 1/2012 |

OTHER PUBLICATIONS

State Monitoring of Lubricating Greases in Roller Bearings, Schaeffler Technologies GmbH & Co. KG, Aug. 2013.

* cited by examiner

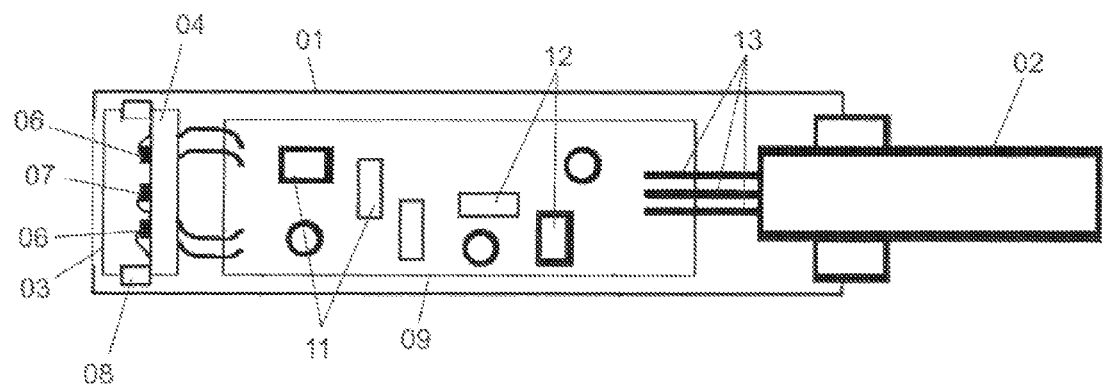

SENSOR UNIT FOR DETERMINING PROPERTIES OF A LUBRICANT AND MACHINE ELEMENT AND MACHINE ASSEMBLY

BACKGROUND

The present invention relates to a sensor unit for determining properties of a lubricant, for example, of a lubricating grease in a rolling bearing. The invention also relates to a machine element with the sensor unit according to the invention and a machine assembly with the machine element according to the invention.

DE 10 2007 042 254 A1 shows a measurement device for analyzing the lubricant in a bearing. This measurement device comprises a transmitter for transmitting infrared radiation that is directed onto a test area and is reflected back from the specimen onto a receiver. The test area is arranged in the interior of the bearing. In particular, IR radiation in the area of combination methods of the C-H oscillations are detected and spectrally analyzed by the receiver. In this way, the lubricant can be continuously monitored during operation and an alarm can be output when the lubricant is to be changed. In the embodiment shown, the transmitter and the receiver are located with a unit for signal conditioning in a common housing. In this housing there are components for signal evaluation by which, for example, calculated properties of the lubricant can be output directly as a digital signal.

DE 10 2010 031 919 A1 teaches a measurement probe for a sensor for analyzing a medium by infrared spectroscopy. With this measurement probe, for example, the lubricant of a bearing can be analyzed. The measurement probe comprises an infrared transmitter and an infrared detector, as well as a reference detector. The infrared detector and the reference detector are arranged on surfaces arranged at a distance from each other. From the infrared transmitter, IR radiation is incident on the medium and is reflected back onto the infrared detector. Furthermore, IR radiation from the infrared transmitter is incident on a mirror surface and is reflected back onto the reference detector. The infrared transmitter and the reference detector are arranged on one carrier. The mirror surface and the infrared detector are formed on opposite sides of a bridge element, wherein the carrier and the bridge element are arranged at a distance from each other. This produces a three-dimensional setup for the components.

From DE 10 2009 037 424 A1, a bearing arrangement is known in which a lubricant sensor transmits information on the state of the bearing to a central receiving station via a transmitter.

DE 10 2010 015 084 A1 shows a sensor part for an infrared sensor for spaced-apart arrangement of an infrared transmitter, an infrared detector, a reference source, and a reference detector.

From the product information sheet "State monitoring of lubricating greases in roller bearings" published by Schaeffler Technologies GmbH and Co. K G, September 2010 and from the product information sheet "FAG GreaseCheck" published by Schaeffler Technologies AG and Co. KG, August 2013, a lubricating grease sensor is known that is provided, in particular, for monitoring the lubricating grease in roller bearings. The lubricating grease sensor comprises a cylindrical sensor head that projects directly into the roller bearing. The sensor head is connected by a cable to evaluation electronics that are arranged in a larger housing at a distance to the sensor head. Analog signals are transmitted from the sensor head to the evaluation electronics. Therefore, the length of the cable must not be greater than one meter. The evaluation electronics in the additional housing makes the use of the lubricating grease sensor more difficult.

SUMMARY

Starting with the known lubricating grease sensor, the object of the present invention is to simplify the use of the lubricating grease sensor.

The specified objective is achieved by a sensor unit and also by a machine element and by a machine arrangement having one or more features of the invention.

The sensor unit according to the invention is used for determining properties of a lubricant. The lubricant is preferably used, in particular, for the purpose of lubricating moving components of a machine element. Here, the sensor unit is preferably constructed for assembly on the machine element or in the machine element. The sensor unit is here preferably constructed for monitoring the lubricant in the machine element.

The sensor unit according to the invention initially comprises a sensor housing that forms an outer shell of the sensor unit. The sensor housing has a window that can be oriented toward the lubricant and preferably can be immersed in the lubricant. The sensor housing is constructed, in particular, for assembly on or in the machine element. The window encloses an interior of the sensor housing. In the sensor housing there is a transmitter for transmitting electromagnetic radiation through the window outside of the sensor housing, namely, onto the lubricant to be examined. The window must be transparent at least for this electromagnetic radiation. In the sensor housing there is also a receiver for receiving electromagnetic radiation that comes through the window. This radiation is any electromagnetic radiation that was transmitted by the transmitter and reflected by the lubricant.

The sensor unit according to the invention further comprises at least one set of evaluation electronics that are arranged in the sensor housing and are connected electrically at least to the receiver. The evaluation electronics are preferably also connected electrically to the transmitter, in particular, in a function as control electronics. The evaluation electronics are constructed for generating at least one digital sensor signal. Consequently, the sensor unit performs not only conditioning, also amplifying of an analog output signal of the receiver. At least one analog-digital conversion of the analog output signal of the receiver is performed, but preferably also an evaluation, so that the digital sensor signal already represents a measured property of the lubricant. The evaluation electronics thus also takes over functions for control and signal conditioning.

The sensor unit according to the invention also comprises an electrical connection that is guided through the sensor housing and is connected electrically to the evaluation electronics in the sensor housing. Consequently, the digital sensor signal can be picked up from outside of the sensor housing by means of the electrical connection. The evaluation electronics and the transmitter are preferably also supplied with power via the electrical connection.

One special advantage of the sensor unit according to the invention is provided in that it does not require a separate evaluation unit that is constructed exclusively for operation as a spaced-apart component of the sensor unit in another housing. Consequently, the sensor unit according to the invention preferably comprises no such separate evaluation unit. Instead, the sensor unit according to the invention preferably comprises a single housing.

In preferred embodiments of the sensor unit according to the invention, the electromagnetic radiation that can be transmitted by the transmitter is formed by infrared radiation. Consequently, the receiver is constructed for receiving infrared radiation. The window is transparent at least for infrared radiation. The infrared radiation is suitable especially for determining properties of a lubricant. The infrared radiation is preferably in the near and/or mid IR range. In principle, other electromagnetic radiation, for example, visible light, could also be used.

The evaluation electronics preferably comprise at least one A/D converter for converting an analog output signal of the receiver into the digital sensor signal.

In preferred embodiments of the sensor unit according to the invention, the receiver and the evaluation electronics are configured such that electromagnetic radiation is to be detected and spectrally analyzed in the infrared range, preferably in the near and/or mid IR range. Through the detection and spectral evaluation of the IR radiation reflected by the lubricant, multiple properties of the lubricant can be determined. For this purpose, the receiver and the evaluation electronics are preferably configured to detect and analyze electromagnetic radiation in the area of the combination methods of the C-H oscillations. In the area of the C-H combination modes, individual absorption lines can be detected that enable conclusions to be drawn on the chemical composition of the lubricant.

The transmitter is preferably connected electrically to the evaluation electronics, wherein the evaluation electronics are configured for controlling the transmitter with different spectral properties of the electromagnetic radiation that can be transmitted. The control of the transmitter for the transmission of electromagnetic radiation with different spectral properties under consideration of the radiation measured on the receiver permits a spectral analysis of the reflection properties of the lubricant.

In preferred embodiments of the sensor unit according to the invention, the evaluation electronics are configured, starting with the control of the transmitter and an output signal of the receiver, to determine at least one signal for representing a property of the lubricant, wherein this signal forms the digital sensor signal or one of the digital sensor signals.

The properties of the lubricant to be determined by a spectral analysis are preferably formed by a state of the lubricant, in particular, by a water content of the lubricant, by a turbidity of the lubricant, by an aging of the lubricant, and/or by a usability of the lubricant. These properties are preferably determined quantitatively. Consequently, the digital sensor signal or one of the digital sensor signals preferably represents a water content of the lubricant, a turbidity of the lubricant, an aging of the lubricant, or a usability of the lubricant.

The sensor unit according to the invention preferably also comprises a temperature sensor arranged in the sensor housing for measuring a temperature of the lubricant. Here, one of the digital sensor signals is preferably formed from an output signal of the temperature sensor. Incidentally, the measured temperature can be additionally used for determining the spectral reflection properties of the lubricant. Here, the evaluation electronics are preferably configured for determining, starting from the control of the transmitter and an output signal of the receiver and also from an output signal of the temperature sensor, at least one signal for representing a property of the lubricant, wherein this signal forms the digital sensor signal or one of the digital sensor signals.

The transmitter is preferably formed by a diode, in particular, an LED.

The electrical connection is preferably formed by a cable. The cable is led out from the sensor housing and is used for the electrical connection of the sensor unit.

One particular advantage of the sensor unit according to the invention is provided in that the output signals of the sensor unit can be transmitted, starting from the sensor unit located in the lubricant, over longer distances, because these signals are digital signals. The sensor heads known from the prior art have an analog output signal that can be transmitted with adequate signal-to-noise ratio only over short distances of less than one meter. The cable of the sensor unit according to the invention is preferably longer than one meter.

The electrical connection preferably comprises exactly one electrical pole constructed for data transmission, e.g., in the form of a wire of a cable, by which the digital sensor signals can be transmitted sequentially. This pole can be designed, for example, as a one-wire bus. The digital sensor signals can also be transmitted, for example, as a PWM signal. A ground potential and a supply voltage can be provided on two additional poles.

The sensor unit according to the invention preferably also comprises a reference receiver, wherein the reference receiver and the receiver are arranged on surfaces that are spaced apart from each other. These surfaces are spaced apart from each other in the direction of the radiation that can be transmitted by the transmitter and are preferably oriented parallel to each other. Here, the sensor unit according to the invention preferably also comprises a mirror surface on which the electromagnetic radiation that can be transmitted by the transmitter can be reflected and can be fed back to the reference receiver. The reference receiver thus receives the electromagnetic radiation transmitted by the transmitter without this radiation having been reflected on the lubricant. By comparing the electromagnetic radiation received with the reference receiver with the electromagnetic radiation received with the receiver, the spectral influence can be determined by the reflection on the lubricant, excluding disturbance variables. The transmitter and the reference receiver are preferably arranged on one carrier, while the receiver and the mirror surface are arranged on opposite flat sides of a bridge element. Here, the mirror surface is turned toward the carrier and the receiver is turned away from the carrier. The carrier and the bridge element are arranged at a distance from each other, wherein this distance is formed in the direction of the radiation that can be transmitted by the transmitter.

Alternatively, the reference receiver can be arranged opposite another transmitter equal to the transmitter.

The transmitter, the receiver, and optionally the reference receiver are preferably formed as DIES.

The sensor housing preferably has a cylindrical base shape, for example, a pen-like base shape. The window is here arranged on one axial end of the cylindrical base shape. A fastener can be located on the other axial end, for example, an external thread with screwed-on nut and with a stop, but preferably there is no such fastener, wherein the fastening of the sensor unit is realized with a positive or non-positive fit by the cylindrical base shape of the sensor housing, for example, with the use of a clamping screw.

The lubricant is preferably formed by a lubricating grease.

The machine element according to the invention has moving components between which a lubricant is arranged. The lubricant is used to reduce the friction between the moving components. The machine element comprises the sensor unit according to the invention, wherein the window of the sensor unit projects into the lubricant. The sensor unit is preferably mounted in or on the machine element.

Preferred embodiments of the machine element according to the invention comprise preferred embodiments of the sensor unit according to the invention.

The machine element is preferably formed by a rolling bearing, but other types of machine elements could also be used.

The machine arrangement according to the invention comprises the machine element according to the invention and a freely programmable computing unit. The electrical connection of the sensor unit is connected electrically to the freely programmable computing unit, so that the digital sensor signal can be processed in the freely programmable computing unit, for example, to determine properties of the lubricant to be examined. Therefore, a program for evaluating the digital sensor signal is preferably loaded on the freely programmable computing unit.

One particular advantage of the sensor unit according to the invention consists namely in that it does not require separate evaluation electronics which are formed exclusively for operation as a set-apart component of the sensor unit in another housing. Instead, the sensor unit according to the invention is preferably operated in combination with a freely programmable computing unit on which a corresponding program for evaluating the digital sensor signal is loaded.

BRIEF DESCRIPTION OF THE DRAWING

Preferred embodiments of the machine arrangement according to the invention comprise preferred embodiments of the machine element according to the invention.

Additional advantages, details, and improvements of the invention are given from the following description of a preferred embodiment of the sensor unit according to the invention with reference to the drawing.

DETAILED DESCRIPTION OF THE PREFERRED EMBODIMENTS

The sole FIG. 1 shows a preferred embodiment of the sensor unit according to the invention in a schematic diagram. The sensor unit comprises, first of all, a cylindrical sensor housing 01 out of which a three-pole cable 02 is guided for the electrical connection of the sensor unit. On the other axial end of the cylindrical shape of the sensor housing 01, a sapphire disk 03 forms a part of the sensor housing 01.

The illustrated sensor unit is used for determining the properties of the lubricating grease that is being used, e.g., in a running rolling bearing. For this purpose, the sensor unit is mounted in the rolling bearing (not shown), wherein the sapphire disk 03 projects into the lubricating grease arranged in the rolling bearing, so that the lubricating grease is located on the sapphire disk 03. The sapphire disk 03 here forms a window of the sensor housing 01.

In the interior of the sensor housing 01, behind the sapphire disk 03 there is a measurement arrangement 04 with infrared transmitters 06 and with an infrared receiver 07. The measurement arrangement 04 is arranged at a distance from the sapphire disk 03 by spacer 08. With the help of the infrared transmitter 06, infrared radiation can be transmitted onto the lubricating grease (not shown) located on the sapphire disk 03, wherein this radiation is then reflected by the lubricating grease back to the infrared receiver 07. The reflection on the lubricating grease changes the spectral composition of the infrared radiation, wherein the changes that occur enable conclusions to be drawn on the properties of the lubricating grease.

In the interior of the sensor housing 01 there is also a circuit board 09 on which control electronics 11 and signal conditioning electronics 12 are arranged. The control electronics 11 and the signal conditioning electronics 12 are connected electrically to the infrared transmitters 06 and to the infrared receiver 07. A targeted control of the infrared transmitter 06 enables spectral evaluation of the infrared radiation reflected by the lubricating grease.

According to the invention, the signal conditioning electronics 12 are arranged together with the measurement arrangement 04 in the sensor housing 01. No other special evaluation electronics in a separate housing are required. Instead, the sensor unit can be connected via the cable 02 directly, for example, to a freely programmable computer that also realizes additional control, regulation, and/or monitoring functions of the machine. In a simple case, the sensor unit can also be connected directly to a signal transmitter that outputs a warning signal to the operator as soon as the lubricating grease is to be changed.

The signal conditioning electronics 12 are formed together with the evaluation electronics 11 for generating a digital sensor signal from the signal of the infrared receiver 07 under consideration of the control of the infrared transmitter 06, wherein this digital signal represents one or more of the determined properties of the lubricating grease. The sensor signal is transmitted, for example, as a one-wire bus signal or as a PWM-coded signal via one of three wires 13 of the cable 02. The two other wires 13 of the cable 02 are provided for a supply voltage and a ground potential.

LIST OF REFERENCE NUMBERS

01 Sensor housing
02 Cable
03 Sapphire disk
04 Measurement arrangement
05 Infrared transmitter
06 Infrared receiver
07 Spacer
08 Circuit board
09 Control electronics
10 -
11 Control electronics
12 Signal conditioning electronics
13 Wires

The invention claimed is:
1. A sensor unit for determining properties of a lubricant, comprising:
   a sensor housing with a window, the window being adapted to be directed onto the lubricant,
   a transmitter arranged in the sensor housing that transmits electromagnetic radiation through the window,
   a receiver arranged in the sensor housing adapted to receive electromagnetic radiation through the window,
   a reference receiver in the sensor housing adapted to receive electromagnetic radiation transmitted by the transmitter without reflection by the lubricant,
   control electronics and signal conditioning electronics arranged in the sensor housing, that are electrically connected to the transmitter and to the receiver and are constructed to generate at least one digital sensor signal, and an electrical connection that is guided through the sensor housing and is electrically connected to the control electronics and the signal conditioning electronics, and the control electronics and the signal conditioning electronics comprise at least one A/D converter that converts an analog output signal of the receiver into the digital sensor signal.

2. The sensor unit according to claim 1, wherein the electromagnetic radiation transmitted by the transmitter is formed by infrared radiation.

3. The sensor unit according to claim 1, wherein the receiver and the control electronics and the signal conditioning electronics are configured to detect and spectrally analyze electromagnetic radiation in the infrared range.

4. The sensor unit according to claim 3, wherein the digital sensor signal represents a state of the lubricant.

5. The sensor unit according to claim 1, wherein the control electronics and the signal conditioning electronics are configured to determine, starting from a control of the transmitter and starting from an output signal of the receiver, at least one signal for representing a property of the lubricant, and said signal forms the digital sensor signal.

6. The sensor unit according to claim 5, wherein the digital sensor signal represents a usability of the lubricant.

7. The sensor unit according to claim 1, further comprising a temperature sensor arranged in the sensor housing that measures a temperature of the lubricant.

8. A machine element comprising moving components, between which a lubricant is arranged, and a sensor unit according to claim 1, and the window of the sensor unit projects into the lubricant.

9. A machine arrangement comprising a machine element according to claim 8 and a programmable computing unit, the electrical connection of the sensor unit is connected electrically to the programmable computing unit.

10. The sensor unit according to claim 1, further comprising a mirror surface which reflects the electromagnetic radiation to the reference receiver.

* * * * *